US009879113B2

(12) United States Patent
Steinbrecher et al.

(10) Patent No.: US 9,879,113 B2
(45) Date of Patent: Jan. 30, 2018

(54) GLYCIDYL ESTERS OF ALPHA, ALPHA BRANCHED ACIDS COMPOSITIONS

(75) Inventors: Christophe Steinbrecher, Ottignies Louvain-la-Neuve (BE); Cedric Le Fevere De Ten Hove, Ottignies Louvain-la-Neuve (BE); Robert Van't Sand, Rotterdam (BE); Denis Heymans, Ottignies Louvain-la-Neuve (BE); Aleksandra Joanna Kotlewska, Rotterdam (NL)

(73) Assignee: HEXION INC., Columbus, OH (US)

( * ) Notice: Subject to any disclaimer, the term of this patent is extended or adjusted under 35 U.S.C. 154(b) by 986 days.

(21) Appl. No.: 13/997,309

(22) PCT Filed: Dec. 16, 2011

(86) PCT No.: PCT/EP2011/006581
§ 371 (c)(1),
(2), (4) Date: Oct. 2, 2013

(87) PCT Pub. No.: WO2012/084266
PCT Pub. Date: Jun. 28, 2012

(65) Prior Publication Data
US 2014/0256906 A1    Sep. 11, 2014

(30) Foreign Application Priority Data

Dec. 22, 2010  (EP) .................................... 10015946

(51) Int. Cl.
| C07D 303/16 | (2006.01) |
| C08G 18/00 | (2006.01) |
| C08G 63/66 | (2006.01) |
| C08G 65/08 | (2006.01) |
| C08G 18/42 | (2006.01) |
| C08G 18/62 | (2006.01) |
| C08G 63/91 | (2006.01) |
| C09D 163/00 | (2006.01) |
| C09D 7/12 | (2006.01) |
| C09D 201/00 | (2006.01) |
| C09D 125/14 | (2006.01) |
| C09D 133/02 | (2006.01) |
| C09D 167/02 | (2006.01) |
| C09D 171/02 | (2006.01) |
| C09D 201/06 | (2006.01) |
| C09D 7/00 | (2006.01) |
| C09J 11/06 | (2006.01) |
| C09J 201/02 | (2006.01) |
| C07C 67/465 | (2006.01) |
| C08K 5/10 | (2006.01) |
| C08F 120/28 | (2006.01) |
| C08F 8/00 | (2006.01) |
| C08L 63/00 | (2006.01) |
| C08K 5/1515 | (2006.01) |
| C08L 33/04 | (2006.01) |
| C08L 67/02 | (2006.01) |
| C09D 133/04 | (2006.01) |
| C08L 71/02 | (2006.01) |
| C08G 59/12 | (2006.01) |
| C09D 4/00 | (2006.01) |

(52) U.S. Cl.
CPC ........... C08G 63/66 (2013.01); C07D 303/16 (2013.01); C08G 18/4291 (2013.01); C08G 59/12 (2013.01); C08K 5/1515 (2013.01); C08L 33/04 (2013.01); C08L 63/00 (2013.01); C08L 67/02 (2013.01); C08L 71/02 (2013.01); C09D 4/00 (2013.01); C09D 133/04 (2013.01); C09D 163/00 (2013.01); C09D 167/02 (2013.01); C09D 171/02 (2013.01)

(58) Field of Classification Search
CPC .. C08G 18/4291; C08G 63/66; C07D 303/16; C08K 5/1515; C07C 53/128; C08L 63/00–63/10; C08L 67/02; C08L 33/04; C08L 71/02; C09D 163/00–163/10; C09D 4/00; C09D 167/02; C09D 133/04; C09D 171/02
See application file for complete search history.

(56) References Cited

U.S. PATENT DOCUMENTS

| 2,831,877 A | 4/1958 | Koch et al. |
| 2,876,241 A | 3/1959 | Koch et al. |
| 2,967,873 A | 1/1961 | Moller et al. |
| 3,053,869 A | 9/1962 | Knights et al. |
| 3,061,621 A | 10/1962 | Koch et al. |
| 3,479,416 A | 11/1969 | Tschopp et al. |
| 3,849,364 A | 11/1974 | Vandenberg |
| 3,979,474 A | 9/1976 | Zerrweck |
| 4,086,151 A | 4/1978 | Stevens et al. |
| 5,051,492 A | 9/1991 | Andre et al. |

(Continued)

FOREIGN PATENT DOCUMENTS

| CN | 1541198 | 10/2004 |
| DE | 102009056187 | 7/2010 |
| EP | 1283226 A1 | 2/2003 |
| JP | 60-32803 | 2/1985 |
| JP | 60262821 | 12/1985 |

(Continued)

OTHER PUBLICATIONS

Kawasaki et al., "Low Pressure Koch Reaction by Cu(Co)n+-H2SO4—H3PO4—H2O Catalyst (Part 4) Structural Analysis of Branched Tert-Nonanoic Acids in the Low Pressure Koch Reaction of Branched Octenes," Sekiyu Gakkaishi, 37 (4), 448-454 (1994).*

(Continued)

*Primary Examiner* — Kregg T Brooks

(57) ABSTRACT

The invention relates to compositions of α,α-branched alkane carboxylic acids glycidyl esters with a define isomeric composition where the sum of the concentration of the blocked and of the highly branched isomers is at least 50%, preferably above 60% and most preferably above 75% on total composition.

6 Claims, No Drawings

(56) References Cited

U.S. PATENT DOCUMENTS

| | | |
|---|---|---|
| 5,681,906 A | 10/1997 | Yezrielev et al. |
| 5,753,756 A | 5/1998 | Aerts |
| 6,087,464 A | 7/2000 | Vijay et al. |
| 6,136,991 A * | 10/2000 | Ryan .................. C07D 303/16 549/541 |
| 6,281,372 B1 * | 8/2001 | Wiese .................. C07C 45/50 554/128 |
| 6,433,217 B1 | 8/2002 | Rosenbrand et al. |
| 6,433,242 B1 | 8/2002 | Weiss et al. |
| 6,592,944 B1 | 7/2003 | Uhlianuk et al. |
| 2003/0149227 A1 | 8/2003 | Okazaki |
| 2003/0149277 A1 | 8/2003 | Okazaki |
| 2005/0176979 A1 * | 8/2005 | Stichter .................. C07C 51/14 554/176 |
| 2007/0082992 A1 | 4/2007 | Heybrechts |
| 2007/0117938 A1 | 5/2007 | Martz et al. |
| 2009/0137751 A1 | 5/2009 | Knott et al. |
| 2012/0095244 A1 | 4/2012 | Gouman et al. |
| 2014/0005300 A1 | 1/2014 | Steinbrecher et al. |
| 2014/0316030 A1 | 10/2014 | Le Fevere et al. |

FOREIGN PATENT DOCUMENTS

| | | |
|---|---|---|
| JP | 4-314797 | 11/1992 |
| JP | 2002526484 A | 8/2002 |
| JP | 2009511669 A | 3/2009 |
| JP | 2009516764 A | 4/2009 |
| WO | WO 96/33245 | 10/1996 |
| WO | WO 99/51659 A1 | 10/1999 |
| WO | WO0125225 | 4/2001 |
| WO | WO0156966 | 8/2001 |
| WO | WO0039180 | 10/2001 |
| WO | WO 2004/059396 A1 | 7/2004 |
| WO | WO 2010/142396 | 12/2010 |

OTHER PUBLICATIONS

Yoneda et al., "Carboxylation of Isobutylene and Related Olefins with Carbon Monoxide and Water in the Presence of BF3—H2O Complex Catalysts," Bull. Jpn. Petrol. Inst. 14, 178 (1972).*

Hampshire, "Glycidyl Ester Based Hydroxylated Polyesters for Coatings and Adhesive Applications" Research Disclosure, Mason Publications, vol. 505, No. 44 (May 1, 2006) GB.

Hampshire, "Glycidyl Ester Based Hydroxylated Polyesters" Research Disclosure, Mason Publications, vol. 563, No. 16 (Mar. 1, 2011) p. 311, GB.

* cited by examiner

GLYCIDYL ESTERS OF ALPHA, ALPHA BRANCHED ACIDS COMPOSITIONS

The present invention relates to a composition of α,α-branched alkane carboxylic acids glycidyl esters with a defined isomeric composition; which can lead for example to improved hardness of the coatings derived thereof.

More in particular the invention relates to the compositions of aliphatic tertiary saturated carboxylic acids or α,α-branched alkane carboxylic acids, which contain 9 or 13 carbon atoms and which provide glycidyl esters with a branching level of the alkyl groups depending on the olefin feedstock used and/or the oligomerisation process thereof, and which is defined as below.

It is generally known from e.g. U.S. Pat. Nos. 2,831,877, 2,876,241, 3,053,869, 2,967,873 and 3,061,621 that mixtures of α,α-branched alkane carboxylic acids can be produced, starting from mono-olefins, such as butenes and isomers such as isobutene, carbon monoxide and water, in the presence of a strong acid.

The glycidyl esters can be obtained according to PCT/EP2010/003334 or the U.S. Pat. No. 6,433,217.

We have discovered that well chosen blend of isomers of the glycidyl ester of, for example, neononanoic acids give different and unexpected performance in combination with some particular polymers such as polyester polyols.

The isomers are described in Table 1 and illustrated in FIG. 1.

We have found that the performance of the glycidyl ester compositions derived from the branched acid is depending on the branching level of the alkyl groups $R^1$, $R^2$ and $R^3$, for example the neononanoic acid has 3, 4 or 5 methyl groups. Highly branched isomers are defined as isomers of neo-acids having at least 5 methyl groups.

Mixture compositions of neononanoic acids glycidyl esters providing for example a high hardness of a coating, is a mixture where the sum of the concentration of the blocked and of the highly branched isomers is at least 50%, preferably above 60% and most preferably above 75% on total composition.

The composition of the glycidyl ester mixture is comprising 2,2-dimethyl 3,3-dimethyl pentanoic acid glycidyl ester and 2-methyl 2-isopropyl 3-methyl butanoic acid glycidyl ester and 2-methyl 2-ethyl 3,3-dimethyl butanoic acid glycidyl ester.

The composition of the glycidyl ester mixture is comprising 2,2-dimethyl 3-methyl 4-methyl pentanoic acid glycidyl ester and 2,2-dimethyl 4,4-dimethyl pentanoic acid glycidyl ester.

The composition of the glycidyl ester mixture in which the sum of the following content of glycidyl ester mixture, comprising 2,2-dimethyl 3,3-dimethyl pentanoic acid glycidyl ester and 2-methyl 2-isopropyl 3-methyl butanoic acid glycidyl ester and 2-methyl 2-ethyl 3,3-dimethyl butanoic acid glycidyl ester, is above 25% weight, preferably above 35% weight and most preferably above 40% weight on total composition.

The composition of the glycidyl ester mixture in which the sum of the following content of glycidyl ester mixture, comprising 2,2-dimethyl 3,3-dimethyl pentanoic acid glycidyl ester and 2-methyl 2-isopropyl 3-methyl butanoic acid glycidyl ester and 2-methyl 2-ethyl 3,3-dimethyl butanoic acid glycidyl ester and 2,2-dimethyl 3-methyl 4-methyl pentanoic acid glycidyl ester and 2,2-dimethyl 4,4-dimethyl pentanoic acid glycidyl ester, is above 40% weight, preferably above 50% weight and most preferably above 65% weight on total composition.

The composition of the glycidyl ester mixture in which the content of 2-methyl 2-ethyl hexanoic acid glycidyl ester is below 40% weight, preferably below 30% weight and most preferably below 20% weight on total composition.

The composition of the glycidyl ester mixture in which the glycidyl ester mixture is comprising 2,2-dimethyl 3,3-dimethyl pentanoic acid glycidyl ester in 1 to 99 weight % and 2-methyl 2-isopropyl 3-methyl butanoic acid glycidyl ester in 1 to 99 weight % and 2-methyl 2-ethyl 3,3-dimethyl butanoic acid glycidyl ester in 1 to 99 weight % on total composition.

A preferred composition of the glycidyl ester mixture in which the glycidyl ester mixture is comprising 2,2-dimethyl 3,3-dimethyl pentanoic acid glycidyl ester in 5 to 50 weight % and 2-methyl 2-isopropyl 3-methyl butanoic acid glycidyl ester in 5 to 50 weight % and 2-methyl 2-ethyl 3,3-dimethyl butanoic acid glycidyl ester in 5 to 50 weight % on total composition.

A further preferred composition of the glycidyl ester mixture in which the glycidyl ester mixture is comprising 2,2-dimethyl 3,3-dimethyl pentanoic acid glycidyl ester in 10 to 14 weight % and 2-methyl 2-isopropyl 3-methyl butanoic acid glycidyl ester in 20 to 28 weight % and 2-methyl 2-ethyl 3,3-dimethyl butanoic acid glycidyl ester in 17 to 22 weight % on total composition.

The composition of the glycidyl ester mixture in which the glycidyl ester mixture is comprising 2,2-dimethyl 3-methyl 4-methyl pentanoic acid glycidyl ester in 1 to 99 weight % and 2,2-dimethyl 4,4-dimethyl pentanoic acid glycidyl ester in 1 to 99 weight %.

A preferred composition of the glycidyl ester mixture in which the glycidyl ester mixture is comprising 2,2-dimethyl 3-methyl 4-methyl pentanoic acid glycidyl ester in 5 to 50 weight % and 2,2-dimethyl 4,4-dimethyl pentanoic acid glycidyl ester in 5 to 50 weight %.

A further preferred composition of the glycidyl ester mixture in which the glycidyl ester mixture is comprising 2,2-dimethyl 3-methyl 4-methyl pentanoic acid glycidyl ester in 10 to 18 weight % and 2,2-dimethyl 4,4-dimethyl pentanoic acid glycidyl ester in 15 to 22 weight %.

The above glycidyl esters compositions can be used for example, is as reactive diluent or as monomer in binder compositions for paints or adhesives.

The glycidyl esters compositions can be used as reactive diluent for epoxy based formulations such as exemplified in the technical brochure of Hexion (Product Bulletin: Cardura N10 The Unique Reactive Diluent).

Other uses of the glycidyl ester are the combinations with polyester polyols, or acrylic polyols, or polyether polyols. The combination with polyester polyols such as the one used in the car industry coating leads to a fast drying coating system with attractive coating properties.

Methods Used

The isomer distribution of neo-acid can be determined using gas chromatography, using a flame ionization detector (FID). 0.5 ml sample is diluted in analytical grade dichloromethane and n-octanol may be used as internal standard. The conditions presented below result in the approximate retention times given in table 1. In that case n-octanol has a retention time of approximately 8.21 minute.

The GC method has the following settings:

Column: CP Wax 58 CB (FFAP), 50 m×0.25 mm, df=0.2 µm

Oven program: 150° C. (1.5 min)–3.5° C./min–250° C. (5 min)=35 min

Carrier gas: Helium

Flow: 2.0 mL/min constant

Split flow: 150 mL/min
Split ratio: 1:75
Injector temp: 250° C.
Detector temp: 325° C.
Injection volume: 1 μL
CP Wax 58 CB is a Gas chromatography column available from Agilent Technologies.

The isomers of neononanoic acid as illustrative example have the structure $(R^1R^2R^3)$—C—COOH where the three R groups are linear or branched alkyl groups having together a total of 7 carbon atoms.

The structures and the retention time, using the above method, of all theoretical possible neononanoic isomers are drawn in FIG. 1 and listed in Table 1.

The isomers content is calculated from the relative peak area of the chromatogram obtained assuming that the response factors of all isomers are the same.

TABLE 1

Structure of all possible neononanoic isomers

|  | R1 | R2 | R3 | Methyl groups | Blocking | Retention time [Minutes] |
|---|---|---|---|---|---|---|
| V901 | Methyl | Methyl | n-pentyl | 3 | No | 8.90 |
| V902 | Methyl | Methyl | 2-pentyl | 4 | Yes | 9.18 |
| V903 | Methyl | Methyl | 2-methyl butyl | 4 | No | 8.6 |
| V904 | Methyl | Methyl | 3-methyl butyl | 4 | No | 8.08 |
| V905 | Methyl | Methyl | 1,1-dimethyl propyl | 5 | Yes | 10.21 |
| V906 | Methyl | Methyl | 1,2-dimethy propyl | 5 | Yes | 9.57 |
| V907 | Methyl | Methyl | 2,2-dimethyl propyl | 5 | No | 8.26 |
| V908 | Methyl | Methyl | 3-pentyl | 4 | Yes | 9.45 |
| V909 | Methyl | Ethyl | n-butyl | 3 | No | 9.28 |
| V910 K1 | Methyl | Ethyl | s-butyl | 4 | Yes | 9.74 |
| V910 K2 | Methyl | Ethyl | s-butyl | 4 | Yes | 9.84 |
| V911 | Methyl | Ethyl | i-butyl | 4 | No | 8.71 |
| V912 | Methyl | Ethyl | t-butyl | 5 | Yes | 9.64 |
| V913 | Methyl | n-propyl | n-propyl | 3 | No | 8.96 |
| V914 | Methyl | n-propyl | i-propyl | 4 | Yes | 9.30 |
| V915 | Methyl | i-propyl | i-propyl | 5 | Yes | 9.74 |
| V916 | Ethyl | Ethyl | n-propyl | 3 | No | 9.44 |
| V917 | Ethyl | Ethyl | i-propyl | 4 | Yes | 10.00 |

The isomer distribution of glycidyl esters of neo-acid can be determined by gas chromatography, using a flame ionization detector (FID). 0.5 ml sample is diluted in analytical grade dichloromethane.

The GC method has the following settings:
Column: CP Wax 58 CB (FFAP), 50 m×0.2 mm, df=0.52 μm
Oven: 175° C. (5 min)–1° C./min–190° C. (0 min)–10° C./min–275° C. (11.5 min)
Flow: 2.0 mL/min, constant flow
Carrier gas: Helium
Split ratio: 1:75
Injection volume: 1 μL
S/SL injector: 250° C.
CP Wax 58 CB is a Gas chromatography column available from Agilent Technologies.

The isomers of glycidyl esters of neononanoic acid as illustrative example have the structure $(R^1R^2R^3)$—C—COO—CH$_2$—CH(O)CH$_2$ where the three R groups are linear or branched alkyl groups having together a total of 7 carbon atoms.

The isomers content is calculated from the relative peak area of the chromatogram obtained assuming that the response factors of all isomers are the same.

GC-MS method can be used to identify the various isomers providing that the analysis is done by a skilled analytical expert.

FIG. 1: Structure of all possible neononanoic isomers

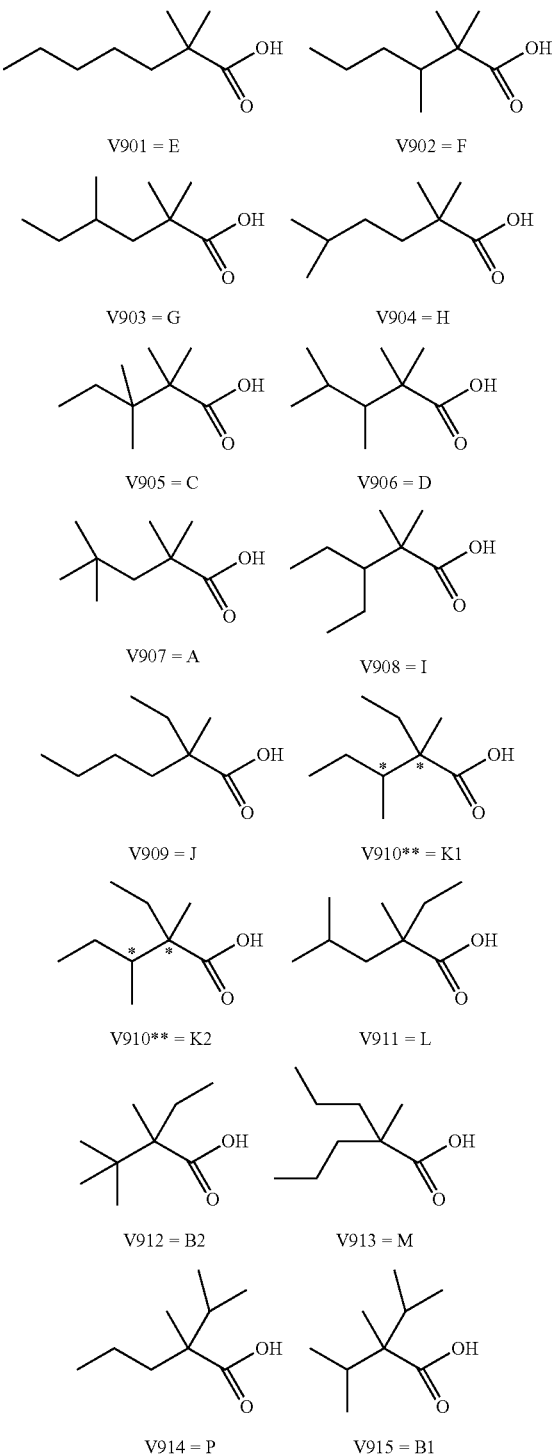

-continued

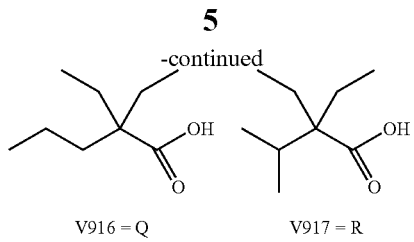

V916 = Q    V917 = R

Test Methods for the Characterization of the Resins

The molecular weights of the resins are measured with gel permeation chromatography (Perkin Elmer/Water) in THF solution using polystyrene standards. Viscosity of the resins are measured with Brookfield viscometer (LVDV-I) at indicated temperature. Solids content are calculated with a function (Ww−Wd)/Ww×100%. Here Ww is the weight of a wet sample, Wd is the weight of the sample after dried in an oven at a temperature 110° C. for 1 hour.

Tg (glass transition temperature) has been determined either with a DSC 7 from Perkin Elmer or with an apparatus from TA Instruments Thermal Analysis. Scan rates were respectively 20 and 10° C./min. Only data obtained in the same experimental conditions have been compared. If not, the temperature difference occurring from the different scanning rate has been proved not significant for the results compared.

Methods for the Characterization of the Clear Coats

Pot-Life

Pot-life is determined by observing the elapsed time for doubling of the initial viscosity at room temperature, usually 24.0±0.5° C. The initial viscosity of the clear coat is defined at 44-46 mPa·s for Part 1 and 93-108 mPa·s for Part 3 measured with Brookfield viscometer.

Application of Clearcoat

Q-panels are used as substrates. Then the panels are cleaned by a fast evaporating solvent methyl ethyl ketone or acetone. For Part 1 the clearcoat is spray-applied on Q-panels covered with basecoat; for Parts 2 & 3 the clearcoat is barcoated directly on Q-panels.

Dust Free Time

The dust free time (DFT) of clear coat is evaluated by vertically dropping a cotton wool ball on a flat substrate from a defined distance. When the cotton ball contacts with the substrate, the substrate is immediately turned over. The dust free time is defined as the time interval at which the cotton wool ball no longer adhered to the substrate.

Hardness Development

Hardness development is followed using pendulum hardness tester with Koenig method.

Blocking Isomers

Whereas the carbon atom in alpha position of the carboxylic acid is always a quaternary carbon atom, the carbon atom(s) in β position can either be tertiary, or quaternary. Neononanoic acids (V9) with a tertiary or a quaternary carbon atom in the β position are defined as blocking isomers (FIGS. 2 and 3).

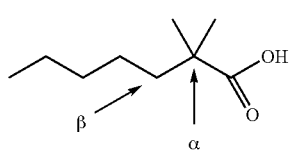

FIG. 2

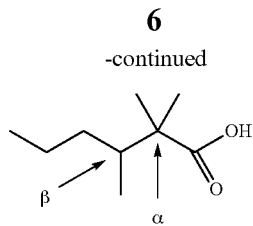

FIG. 3

FIG. 2: Example of a Non-blocked V9 Structure
FIG. 3: Example of a Blocked V9 Structure β

The use of the glycidyl esters compositions, discussed here above, is as reactive diluent or as monomer in binder compositions for paints and adhesives. These uses can be based on a polyester polyol resin comprising the above composition glycidyl ester and/or an acrylic polyol resin comprising the above composition glycidyl ester and/or a polyether polyol resin comprising the above composition glycidyl ester and/or an epoxy resin formulation comprising the above composition glycidyl ester.

EXAMPLES

Chemicals Used
Cardura™ E10: available from Momentive Specialty Chemicals
Neononanoic glycidyl ester from Momentive Specialty Chemicals
GE9S: neononanoic glycidyl ester of composition A (see table 2 below)
GE9H: neononanoic glycidyl ester of composition B (see table 2 below)
Neononanoic glycidyl ester of composition C (see table 2 below)
Neononanoic glycidyl ester of composition D (see table 2 below)
Neononanoic glycidyl ester of composition E (see table 2 below)

TABLE 2

Composition of the neononanoic glycidyl ester
(according to the described gas chromatography
method for glycidyl esters of neo-acid)

| Glycidyl ester of acid V9XX (described in Table 1) | A (%) | B (%) | C (%) | D (%) | E (%) |
|---|---|---|---|---|---|
| V901 | 6.5 | 0.1 | 3.7 | 0.1 | 0.1 |
| V902 | 0.6 | 2.55 | 0.6 | 2.4 | 2.65 |
| V903 | 1.1 | 0.7 | 0.3 | 1.0 | 0.4 |
| V904 | 0.8 | 1 | 0.1 | 2.2 | 0.4 |
| V905 | 0.2 | 13.1 | 0.5 | 4.1 | 14.5 |
| V906 | 0.4 | 11.6 | 0.4 | 9.6 | 12.6 |
| V907 | 0.2 | 15.4 | 0.1 | 36.4 | 5.6 |
| V908 | 0.1 | 0 | 0.1 | 0.0 | 0.0 |
| V909 | 54.8 | 2.55 | 52.8 | 2.4 | 2.65 |
| V910 K1 | 7.8 | 0 | 10.0 | 0.0 | 0.0 |
| V910 K2 | 7.7 | 0.6 | 12.8 | 0.4 | 0.7 |
| V911 | 2.4 | 1.2 | 0.7 | 2.0 | 0.8 |
| V912 | 0.0 | 28.3 | 0.0 | 22.4 | 33.5 |
| V913 | 6.8 | 0.1 | 6.4 | 0.1 | 0.1 |
| V914 | 4.5 | 0 | 3.8 | 0.0 | 0.0 |
| V915 | 0.6 | 22.3 | 0.6 | 16.8 | 25.3 |
| V916 | 4.4 | 0.1 | 5.2 | 0.1 | 0.1 |
| V917 | 1.1 | 0.4 | 2.1 | 0.1 | 0.4 |

GE5: glycidyl ester of pivalic acid obtained by reaction of the acid with epichlorhydrin.
Ethylene glycol from Aldrich
Monopentaerythritol: available from Sigma-Aldrich Methylhexahydrophtalic anhydride: available from Sigma-Aldrich
Boron trifluoride diethyl etherate (BF3.OEt2) from Aldrich
Acrylic acid: available from Sigma-Aldrich
Hydroxyethyl methacrylate: available from Sigma-Aldrich
Styrene: available from Sigma-Aldrich
2-Ethylhexyl acrylate: available from Sigma-Aldrich
Methyl methacrylate: available from Sigma-Aldrich
Butyl acrylate: available from Sigma-Aldrich
Xylene
Di-t-Amyl Peroxide is Luperox DTA from Arkema
tert-Butyl peroxy-3,5,5-trimethylhexanoate: available from Akzo Nobel
n-Butyl Acetate from Aldrich
Dichloromethane from Biosolve
Thinner: A: is a mixture of Xylene 50 wt %, Toluene 30 wt %, ShellsolA 10 wt %, 2-Ethoxyethylacetate 10 wt %. Thinner B: is butyl acetate
Curing agents, HDI: 1,6-hexamethylene diisocyanate trimer, Desmodur N3390 BA from Bayer Material Science or Tolonate HDT LV2 from Perstorp
Leveling agent: 'BYK 10 wt %' which is BYK-331 diluted at 10% in butyl acetate
Catalyst: 'DBTDL 1 wt %' which is Dibutyl Tin Dilaurate diluted at 1 wt % in butyl acetate Example 1 Comparative The following constituents were charged to a reaction vessel equipped with a stirrer, a condenser and a thermometer: 92.4 grams of GE9S, 24.0 grams of Butyl Acetate. That initial reactor charge has been heated up to 135° C. Then, the following mixture was added over a period of 1 h20 while keeping the temperature constant: 30.7 grams of acrylic acid, 1.2 grams of Di-t-Amyl Peroxide, 12.0 grams of n-Butyl Acetate. After further adding 1.2 grams of Di-t-Amyl Peroxide and 20.4 grams of n-Butyl Acetate, a post-cooking was pursued at 135° C. for 1 h. The acrylic polyol had a molecular weight (Mw) of 11400 Daltons and a Tg of about −10° C.

Example 2

The following constituents were charged to a reaction vessel equipped with a stirrer, a condenser and a thermometer: 92.4 grams of GE9H, 24.0 grams of Butyl Acetate. That initial reactor charge has been heated up to 135° C. Then, the following mixture was added over a period of 1 h18 while keeping the temperature constant: 30.2 grams of acrylic acid, 1.2 grams of Di-t-Amyl Peroxide, 12.0 grams of n-Butyl Acetate. After further adding 1.2 grams of Di-t-Amyl Peroxide and 20.4 grams of n-Butyl Acetate, a post-cooking was pursued at 135° C. for 1 h. The acrylic polyol had a molecular weight (Mw) of 8600 Daltons and a Tg of about +26° C.

Observations: Tg of acrylic polyols is impacted by the composition of the neononanoic glycidyl ester (see examples 1, 2).

Example 3

The Adducts of Glycidyl Neononanoate, GE9H and Acrylic Acid or Methacrylic Acid
The adducts of Glycidyl neononanoate GE9H (see table 3) with acrylic acid (ACE-adduct) and with methacrylic acid (MACE-adduct) are acrylic monomers that can be used to formulate hydroxyl functional (meth)acrylic polymers.

TABLE 3

Compositions of the adducts intakes in parts by weight

|  | Acrylic acid adduct | Meth acrylic acid adduct |
|---|---|---|
| Initial reactor charge |  |  |
| GE9H | 250 | 250 |
| Acrylic acid | 80 |  |
| Methacrylic acid |  | 96.5 |
| Radical Inhibitor |  |  |
| 4-Methoxy phenol | 0.463 | 0.463 |
| Catalyst |  |  |
| DABCO T9 (0.07 wt % on Glycidyl ester) | 0.175 | 0.175 |

DABCO T9 and 4-Methoxy phenol (185 ppm calculated on glycidyl ester weight), are charged to the reactor.
The reaction is performed under air flow (in order to recycle the radical inhibitor).
The reactor charge is heated slowly under constant stirring to about 80° C., where an exothermic reaction starts, increasing the temperature to about 100° C.
The temperature of 100° C. is maintained, until an Epoxy Group Content below 30 meq/kg is reached. The reaction mixture is cooled to room temperature.

Example 4

Acrylic Resins for High Solids Automotive Refinish Clearcoats

A glass reactor equipped with stirrer was flushed with nitrogen, and the initial reactor charge (see table 4) heated to 160° C. The monomer mixture including the initiator was then gradually added to the reactor via a pump over 4 hours at this temperature. Additional initiator was then fed into the reactor during another period of 1 hour at 160° C. Finally the polymer is cooled down to 135° C. and diluted to a solids content of about 68% with xylene.

TABLE 4

Acrylic resins recipe

|  | Weight % | in Reactor 1 L (g) |
|---|---|---|
| Initial Reactor Charge |  |  |
| GE9H or GE9S (Comparative) | 28.2 | 169.1 |
| Xylene | 2.7 | 16.2 |
| Feeding materials |  |  |
| Acrylic acid | 10 | 59.8 |
| Hydroxy ethyl methacrylate | 16.0 | 96.0 |
| Styrene | 30.0 | 180.0 |
| Methyl methacrylate | 15.8 | 95.0 |
| Di t-Amyl peroxide | 4.0 | 24.0 |
| Xylene | 8.3 | 49.8 |
| Post cooking |  |  |
| Di t-Amyl peroxide | 1.0 | 6.0 |
| Xylene | 3.0 | 18.0 |
| Solvent adding at 130° C. |  |  |
| Xylene | 50.8 | 305.0 |
| Final solids content | 61.8% |  |
| Hydroxyl content | 4.12% |  |

Example 5

Clear Coats for Automotive Refinish
Solvents were blended to yield a thinner mixture of the following composition (table 5):

TABLE 5

Thinner composition
A clearcoat was then formulated (table 6) with the following ingredients (parts by weight):

| Thinner | Weight % in solvent blend, theory |
|---|---|
| Toluene | 30.1% |
| ShellSolA | 34.9% |
| 2-ethoxyethyl acetate | 10.0% |
| n-Butyl acetate | 25.0% |
| Total | 100% |

TABLE 6

Clearcoat formulation

| Resin of example ex 4 | Desmodur N3390 | BYK 10 wt % in ButAc | DBTDL 1 wt % in ButAc | Thinner |
|---|---|---|---|---|
| 80.1 | 27.01 | 0.53 | 1.17 | 40.45 |

| Clearcoat properties | GE9H | GE9S (Comparative) |
|---|---|---|
| Volatile organic content | 480 g/l | 481 g/l |
| Initial viscosity | 54 cP | 54 cP |
| Dust free time | 12 minutes | 14.5 minutes |
| Koenig Hardness after 6 hours | 8.3 s | 7.1 s |

Example 6

Acrylic Resins for First Finish Automotive Topcoats
GE9H Based (28%) Acrylic Polymers for Medium Solids First-finish Clear Coats A reactor for acrylic polyols is flushed with nitrogen and the initial reactor charge (see table 7) heated to 140° C. At this temperature the monomer mixture including the initiator is added over 4 hours to the reactor via a pump. Additional initiator is fed into the reactor during one hour, and then the mixture is kept at 140° C. to complete the conversion in a post reaction. Finally the polymer is cooled down and diluted with butyl acetate to a solids content of about 60%.

TABLE 7

Acrylic resins recipe

| | Intakes (parts by weight) |
|---|---|
| Initial reactor charge | |
| GE9H | 164.40 |
| Xylene | 147.84 |
| Monomer mixture | |
| Acrylic acid | 53.11 |
| Butyl methacrylate | 76.88 |
| Butyl acrylate | 48.82 |

TABLE 7-continued

Acrylic resins recipe

| | Intakes (parts by weight) |
|---|---|
| Hydroxy-ethyl methacrylate | 27.20 |
| Styrene | 177.41 |
| Methyl methacrylate | 47.31 |
| Initiator | |
| Di-tert.-amyl peroxide (DTAP) | 8.87 |
| Post addition | |
| Di-tert.-amyl peroxide | 5.91 |
| Solvent (to dilute to 60% solids) | |
| Butyl acetate | 246.00 |
| Total | 1000.0 |

Clear Lacquer Formulation
Clear lacquers are formulated (see table 8) from the acrylic polymers by addition of Cymel 1158 (curing agent from CYTEC), and solvent to dilute to spray viscosity. The acidity of the polymer is sufficient to catalyze the curing process, therefore no additional acid catalyst is added. The lacquer is stirred well to obtain a homogeneous composition.

TABLE 8

Clear lacquer formulations and properties of the polymers

| | Intakes (part by weight) |
|---|---|
| Ingredients | |
| Acrylic polymer | 60.0 |
| Cymel 1158 | 8.8 |
| Butyl acetate (to application viscosity) | 24.1 |
| Properties | |
| Solids content [% m/m] | 45.3 |
| Density [g/ml] | 0.97 |
| VOC [g/l] | 531 |

Application and Cure
The coatings are applied with a barcoater on Q-panels to achieve a dry film thickness of about 40 μm. The systems are flashed-off at room temperature for 15 minutes, then baked at 140° C. for 30 minutes. Tests on the cured systems are carried out after 1 day at 23° C.

Example 7

In a reactor equipped with an anchor stirrer, a thermometer, condenser and monomer/initiator feeding system, 188.6 g of GE9H and 90 g of ethoxypropanol (EPR) were loaded and heated to about 150° C. (see table 9). A mixture of 52 g of hydroxyethylmethacrylate (HEMA), 160 g of styrene, 68 g of acrylic acid (AA), 10 g of dicumylperoxide (DCP), 37.7 g of GE9H and 40 g of ethoxypropanol (EPR) were added over 2 hours 30 minutes to the reactor while keeping its content at 150° C. After the feed, the reactor content was held for 30 minutes at this temperature. After the 30 minutes hold period, 108 g of HEMA, 30 g of AA, 142 g of isobutyl methacrylate (IBMA), 5 g of DCP and 45 grams of EPR were added over 2 hours and 30 minutes at about 150° C. followed by a rinsing step for the feed system with 5 g of EPR. After the rinsing step, the content of the reactor was held for 2 hours at 150° C. The reactor content was cooled down to 100° C. and 100 parts of EPR were distilled off at atmospheric pressure.

The polyacrylate polyol has a solids content of the solution of 90% by weight.

TABLE 9

Composition of polyol

| Materials | | Intake (g) |
|---|---|---|
| Initial charge | EPR | 90 |
| | GE9H | 188.6 |
| Monomer Addition 1 | AA | 68 |
| | Styrene | 160 |
| | GE9H | 37.7 |
| | HEMA | 52 |
| | EPR | 40 |
| | DCP | 10 |
| Monomer Addition 2 | AA | 30 |
| | IBMA | 142 |
| | HEMA | 108 |
| | DCP | 5 |
| | EPR | 45 |
| TOTAL | | 976.3 |

Example 8 Comparative

The following constituents were charged to a reaction vessel: 0.7153 grams of a neononanoic glycidyl ester of composition C, 0.5958 grams of hexahydro-4-methylphthalic anhydride, 0.0014 grams of ethylene glycol. The reaction took place for 3 to 4 days at 140° C. The sample has been dried by evaporation. The polyester had a molecular weight (Mn) of 4700 Daltons and a Tg of +18.8° C.

Example 9

The following constituents were charged to a reaction vessel: 0.5823 grams of a neononanoic glycidyl ester of composition D, 0.4775 grams of hexahydro-4-methylphthalic anhydride, 0.0011 grams of ethylene glycol, 0.2841 grams of n-Butyl Acetate. The reaction took place for 3 to 4 days at 120-140° C. and the solvent was then thoroughly removed by evaporation. The polyester had a molecular weight (Mn) of 5000 Daltons and a Tg of +43.7° C.

Example 10

The following constituents were charged to a reaction vessel: 0.5846 grams of a neononanoic glycidyl ester of composition E, 0.4786 grams of hexahydro-4-methylphthalic anhydride, 0.0011 grams of ethylene glycol, 0.2847 grams of n-Butyl Acetate. The reaction took place for 3 to 4 days at 120-140° C. and the solvent was then thoroughly removed by evaporation. The polyester had a molecular weight (Mn) of 3800 Daltons and a Tg of +48.1° C.

Observations: Tg of polyesters is impacted by the composition of the neononanoic glycidyl ester (see examples 8, 9, 10).

The resins of the examples can be formulated in coating compositions such as 2K (polyurethane) with a low VOC (volatile organic compound) level and still providing and excellent appearance.

Example 11 Comparative

Monopentaerythritol, methylhexahydrophthalic anhydride and n-Butyl Acetate (see 1°/in Table 10) were charged to a reaction vessel and heated at 140° C. until complete conversion. Cardura E10P (see 1°/in Table 10) was then dropwise added and the reaction pursued until acceptable acid value. The polyester had a solid content of 76.0 wt %. At a suitable temperature, Cardura E10P and xylene (see 2°/in Table 10) were then added. The mixture was heated to about 157° C. and the monomers, radical initiator and solvent (see 3°/in Table 10) were fed for 6 hours at that temperature. A post-cooking (1 h) then took place with additional radical initiator (see 4°/in Table 10). After further addition of n-butyl acetate (see 5°/in Table 10), the final resin had a solid content of 66.2 wt %.

Example 12

Recipe of example 11 was used with the amount indicated in table 10 while using GE9H instead of Cardura E10P for the polyester cooking. The intermediate polyester and the final resin had a solid content of 78.4 wt % and 66.8 wt %, respectively.

Example 13

Recipe of example 12 was used with the amount indicated in table 10 while using GE9H instead of Cardura E10P for the acrylic polyol cooking. The intermediate polyester and the final resin had a solid content of 78.4 wt % and 68.3 wt %, respectively.

TABLE 10

Constituents for the polyester based acrylic polyol cooking

| | Example 11 | Example 12 | Example 13 |
|---|---|---|---|
| 1°/Polyester cooking, constituent (g) | | | |
| Monopentaerythritol | 4.0 | 4.2 | 3.4 |
| Methylhexahydrophthalic anhydride | 15.2 | 15.9 | 12.7 |
| n-Butyl acetate | 10.0 | 10.4 | 8.3 |
| Cardura E10P | 22.3 | | |
| GE9H | | 21.9 | 17.5 |
| 2°/Acrylic polyol cooking, initial reactor charge (g) | | | |
| Polyester (from above) | 51.5 | 52.3 | 41.8 |
| Cardura E10P | 33.2 | 31.3 | — |
| GE9H | — | — | 24.9 |
| Xylene | 3.6 | 3.4 | 2.9 |
| 3°/Acrylic polyol cooking, feeding material (g) | | | |
| Acrylic Acid | 9.5 | 9.0 | 7.6 |
| Hydroxyethyl methacrylate | 23.9 | 22.5 | 19.0 |
| Styrene | 39.8 | 37.5 | 31.7 |
| Butyl Acrylate | 0.0 | 0.0 | 0.8 |
| Methyl methacrylate | 26.3 | 24.8 | 21.6 |
| Xylene | 11.0 | 10.4 | 8.8 |
| Di-t-Amyl Peroxide | 5.3 | 5.0 | 4.2 |
| 4°/Acrylic polyol post cooking, feeding material (g) | | | |
| Di-t-Amyl Peroxide | 1.3 | 1.3 | 1.1 |
| 5°/Acrylic polyol solid content adjustment, solvent adding (g) | | | |
| n-Butyl acetate | 55.7 | 52.6 | 44.4 |

Formulation of the Clear Coats

A clear coat is formulated with one of the polyester based acrylic polyol (from examples 11, 12 or 13, the curing agent (HDI, Desmodur N3390), the thinner, the levelling agent (BYK-331) and the catalyst (dibutyltin dilaurate, DBTDL) according to the amounts indicated in table 11.

TABLE 11

| CE-Example | Binder (ID) | Binder (g) | HDI (g) | BYK 10 wt % (g) | DBTDL 1 wt % (g) | Thinner A (g) |
|---|---|---|---|---|---|---|
| CE-11 | From Example 11 | 92.1 | 34.7 | 0.67 | 1.47 | 37.2 |
| CE-12 | From Example 12 | 91.3 | 36.0 | 0.66 | 1.46 | 37.4 |
| CE-13 | From Example 13 | 91.3 | 36.9 | 0.68 | 1.50 | 39.7 |

Characterization of the Clear Coats

The clearcoat formulations (from table 11) are barcoat applied on degreased Q-panel. The panels are dried at room temperature, optionally with a preliminary stoving at 60° C. for 30 min. Clear coats have been characterized among others by measuring the dust free time and Koenig hardness development (see table 12).

TABLE 12

Clear coats, drying (curing) properties

| | CE-11 | CE-12 | CE-13 |
|---|---|---|---|
| 1°/Dust free time (Room temperature drying panels) (min) | | | |
| Dust free time (min) | 39 | 35 | 24 |
| 2°/Koenig Hardness (Room temperature drying panels) (sec) | | | |
| 6 hours | 3 | 4 | 7 |
| 24 hours | 31 | 38 | 49 |
| 7 days | 156 | 167 | 179 |
| 3°/Koenig Hardness (Stoved Q panels) (sec) | | | |
| Out of the oven | 12 | 15 | 24 |
| 6 hours | 15 | 18 | 29 |
| 24 hours | 48 | 55 | 67 |
| 7 days | 178 | 180 | 190 |

Observation (see table 12): significant improvement (lower dust free time and quicker hardness development) is observed when replacing Cardura E10P by GE9H for the polyester cooking. Improvement is even more significant when Cardura E10P is complementary replaced by GE9H for the acrylic polyol cooking.

Example 14 Comparative

Monopentaerythritol/Methylhexahydrophtalic anhydride/ GE9S (1/3/3 molar ratio)=CE-GE9S 80.4 g amount of butylacetate, 68.3 g of monopentaerythritol, 258.2 g of methylhexahydrophthalic anhydride are loaded in a glass reactor and heated to reflux until complete dissolution. Afterwards, the temperature is decreased down to 120° C. and 333.0 g of GE9S are added over about one hour. The cooking is pursued at 120° C. for the time needed to decrease epoxy group content and acid value down to an acid value below 15 mg KOH/g. Then, further 82.4 g of butylacetate are added. Test results are indicated in table 13.

Example 15a

Monopentaerythritol/Methylhexahydrophtalic anhydride/ GE9H (1/3/3 molar ratio)=CE-GE9Ha 80.4 g amount of butylacetate, 68.3 g of monopentaerythritol, 258.2 g of methylhexahydrophthalic anhydride are loaded in a glass reactor and heated to reflux until complete dissolution. Afterwards, the temperature is decreased down to 120° C. and 337.1 g of GE9H are added over about one hour. The cooking is pursued at 120° C. for the time needed to decrease epoxy group content and acid value down to an acid value below 15 mg KOH/g. Then, further 83.4 g of butylacetate are added. Test results are indicated in table 13.

Example 15b

Monopentaerythritol/Methylhexahydrophtalic Anhydride/ GE9H (1/3/3 Molar Ratio)=CE-GE9Hb CE-GE9Hb is a duplication of Example 15a performed in very close experimental conditions.

Example 16a Comparative According to EP 0996657

Monopentaerythritol/Methylhexahydrophtalic Anhydride/ GE5 (1/3/3 Molar Ratio) CE-GE5a 71.3 g amount of butylacetate, 60.5 g of monopentaerythritol, 228.90 g of methylhexahydrophthalic anhydride are loaded in a glass reactor and heated to reflux until complete dissolution. Afterwards, the temperature is decreased down to 120° C. and 214.3 g of GE5 are added over about one hour. The cooking is pursued at 120° C. for the time needed to decrease epoxy group content and acid value down to an acid value below 15 mg KOH/g. Then, further 52.1 g of butylacetate are added. Test results are indicated in table 13.

Example 16b Comparative According to EP 0996657

Monopentaerythritol/Methylhexahydrophtalic Anhydride/ GE5 (1/3/3 Molar Ratio) CE-GE5b CE-GE5b is a duplication of comparative example 16a performed in very close experimental conditions except for the higher amount of butylacetate added at the end of the reaction.

TABLE 13

Polyesters characterization

| Polyester resin | SC (%) | Mw (Da) | Mn (Da) | Mw/Mn (PDI) | Viscosity (cP) |
|---|---|---|---|---|---|
| CE-GE9S | 78.6 | 974 | 919 | 1.06 | 2450 (25.9° C.) |
| CE-GE9Ha | 80.0 | 921 | 877 | 1.05 | 6220 (25.9° C.) |
| CE-GE9Hb | 80.0 | 1014 | 975 | 1.04 | 11740 (21.6° C.) |
| CE-GE5a | 79.3 | 914 | 886 | 1.03 | 5080 (26.0° C.) |
| CE-GE5b | 68.3 | 1177 | 1122 | 1.05 | 102.3 (22.0° C.) |

SC: solids content

Example 17 Comparative

Acrylic Resin Synthesis

Cardura™ E10 Based Acrylic Polyol Resin: Acryl-CE(10)

105.0 g amount of CE10 (Cardura™ E10-glycidyl ester of Versatic acid) and 131.6 g of Shellsol A are loaded in a glass reactor and heated up to 157.5° C. Then, a mixture of monomers (37.4 g acrylic acid, 107.9 g hydroxyethyl methacrylate, 180.0 g styrene, 100.2 g butyl acrylate, 69.6 g methyl methacrylate) and initiator (12.0 g Di-tert-butyl peroxide) is fed into the reactor at a constant rate in 5 hours. Then post cooking started: a mixture of 6.0 g Di-tert-butyl peroxide and 18.0 g n-butyl acetate is fed into the reactor at a constant rate in 0.5 hour, then temperature maintained at about 157.5° C. for a further 0.5 hour. Finally, 183.2 g of n-butyl acetate is added under stirring to achieve a polyol resin with the target solids content. Test results are indicated in table 14.

TABLE 14

Acryl-CE(10) characterization

| Acryl- | SC (%)-measured | Mw (Da) | Mn (Da) | Mw/Mn (PDI) |
|---|---|---|---|---|
| CE(10) | 65.2 | 5094 | 2629 | 1.94 |

Three types of formulations have been prepared:

Blend Acryl-CE(10) blend with CE-GEx polyester with Desmodur as hardener (Part 1)

CE-GEx polyester alone with Tolonate HDT LV2 as hardener (0.03 wt % DBTDL)(Part 2)

CE-GEx polyester alone with Tolonate HDT LV2 as hardener (0.09 wt % DBTDL) (Part 3)

Part 1: CE-GEx Polyesters Blend with Acryl-CE(10) Formulation

TABLE 15

Clear coats, formulations

| CE-GEx | Binder 1 (g) | Binder 2 (g) | HDI (g) | BYK 10 wt % (g) | DBTDL 1 wt % (g) | Thinner A (g) |
|---|---|---|---|---|---|---|
| GE9Hb | 71.6 | 16.9 | 31.2 | 0.63 | 1.39 | 86.33 |
| GE5b | 79.1 | 12.4 | 31.2 | 0.63 | 1.39 | 89.30 |

Binder 1: Acryl-CE(10)
Binder 2: CE-GEx polyesters

Part 2—CE-GEx Polyesters Alone, No Acryl-CE(10) Formulation (0.03 wt % DBTDL)

TABLE 16

Clear coats, formulations

| CE-GEx | Binder 2 (g) | HDI (g) | BYK 10 wt % (g) | DBTDL 1 wt % (g) | Thinner B (g) |
|---|---|---|---|---|---|
| GE9S | 80.0 | 36.56 | 0.72 | 3.15 | 89.75 |
| GE9Ha | 80.4 | 37.27 | 0.73 | 3.20 | 87.83 |
| GE5a | 79.9 | 43.18 | 0.76 | 3.36 | 94.82 |

Part 3—CE-GEx Polyesters Alone, No Acryl-CE(10) Formulation (0.09 wt % DBTDL)

TABLE 17

Clear coats, formulations

| CE-GEx | Binder 2 (g) | HDI (g) | BYK 10 wt % (g) | DBTDL 1 wt % (g) | Thinner B (g) |
|---|---|---|---|---|---|
| GE9Ha | 60.0 | 28.10 | 0.54 | 7.18 | 15.40 |
| GE5a | 59.8 | 32.54 | 0.57 | 7.57 | 17.79 |

Characterization of the Clear Coats

The clearcoat formulations are barcoat applied on degreased Q-panel for Parts 2 & 3; sprayed for the Part 1 on Q-panel with a basecoat. The panels are dried at room temperature, optionally with a preliminary stoving at 60° C. for 30 min.

Part 1—CE-GEx Polyesters Blend with Acryl-CE(10)/Room Temperature curing

TABLE 18

Clear coats, performances

| CE-GEx | SC (%) | Potlife (h) | Drying conditions | DFT (min) Cotton Balls |
|---|---|---|---|---|
| GE9Hb | 47.1 | 4.5 | RT | 15 |
| GE5b | 46.2 | 4.0 | RT | 19 |

SC: solids content,
RT: room temperature

Part 2—CE-GEx Polyesters Alone, No Acryl-CE(10)/Room Temperature Curing and Room Temperature Drying after Stoving

TABLE 19

Clear coats, performances

| CE-GEx | SC (%) | Drying conditions | DFT (min) Cotton Balls | Koenig Hardness (s) 6 h | 24 h | 7 d |
|---|---|---|---|---|---|---|
| GE9S | 48.4 | RT | 223 | 3 | 17 | 159 |
| GE9Ha | 49.2 | RT | 91 | 3 | 36 | 212 |
| GE5a | 49.5 | RT | 114 | 1 | 29 | 216 |
| GE9S | 48.4 | Stoving 30 min/60° C. | Dust free out of oven | 4 | 44 | 174 |
| GE9Ha | 49.2 | Stoving 30 min/60° C. | Dust free out of oven | 10 | 55 | 211 |
| GE5a | 49.5 | Stoving 30 min/60° C. | Dust free out of oven | 6 | 49 | 216 |

Part 3—CE-GEx Polyesters Alone, No Acryl-CE(10)/ Room Temperature Curing and Room Temperature Drying after Stoving (0.09 wt % DBTDL)

TABLE 20

Clear coats, performances

| CE-GEx | SC (%) | Pot-life (min) | Drying conditions | DFT (min) Cotton Balls | Koenig Hardness (s) | | |
|---|---|---|---|---|---|---|---|
| | | | | | 6 h | 24 h | 7 d |
| GE9Ha | 69.8 | 42.4 | RT | 47 | 3 | 66 | 193 |
| GE5a | 68.5 | 61.3 | RT | 73 | 3 | 55 | 191 |
| GE9Ha | 69.8 | 42.4 | Stoving 30 min/60° C. | Dust free out of oven | 29 | 102 | 210 |
| GE5a | 68.5 | 61.3 | Stoving 30 min/60° C. | Dust free out of oven | 12 | 69 | 205 |

Observations

Part 1

The potlife is about the same, the dust free time is shorter for GE9Hb vs. GE5b.

Part 2

The 24 h hardness order GE9H, GE5 and GE9S and the dust free time at room temperature is the best for GE9H.

Part 3

The hardness development is the best for GE9H at room temperature and heat cure, the dust free time at room temperature is quicker for GE9H than for GE5; and with a volatile organic content of 300 g/l.

Example 18

The following constituents were charged to a reaction vessel: 2.5500 grams of a neononanoic glycidyl ester of composition D, 1.1571 grams of dichloromethane, 0.0137 grams of boron trifluoride diethyl etherate. The reaction took place for 3 days at room temperature and the solvent was then thoroughly removed by evaporation. The polyether had a molecular weight (Mw) of 1900 Daltons and a Tg of −40.5° C.

Example 19 Comparative

The following constituents were charged to a reaction vessel: 2.5438 grams of a neononanoic glycidyl ester of composition C, 1.0150 grams of dichloromethane, 0.0128 grams of boron trifluoride diethyl etherate. The reaction took place for 3 days at room temperature and the solvent was then thoroughly removed by evaporation. The polyether had a molecular weight (Mw) of 1500 Daltons and a Tg of −51.1° C.

Observations: Tg of the modified polyether resin is impacted by the composition of the neononanoic glycidyl ester (see examples 18, 19).

Example 20

Polyether Resin

The following constituents were charged to a reaction vessel equipped with a stirrer, a thermometer and a condenser: 134 grams of di-Trimethylol propane (DTMP), 900 grams of glycidyl neononanoate, GE9H, 135.5 grams of n-butylacetate (BAC) and 2.5 grams of Tin 2 Octoate. The mixture was heated to its reflux temperature of about 180° C. for about 4 hours till the glycidyl neononaoate was converted to an epoxy group content of less than 0.12 mg/g. After cooling down the polyether had a solids content of about 88%.

Example 21 Comparative

Polyether Resin

The following constituents were charged to a reaction vessel equipped with a stirrer, a thermometer and a condenser: 28.8 grams of monopentaerythritol, 201.5 grams of Cardura E10P, 19.4 grams of n-butylacetate and 0.3552 grams of Tin (II) 2-ethylhexanoate. The mixture was heated to a temperature of about 180° C. for about 6 hours till the Cardura E10P was converted to an epoxy group content of about 25 mmol/kg. After cooling down the polyether had a solids content of about 94%.

Example 22 Comparative

Polyether Resin

The following constituents were charged to a reaction vessel equipped with a stirrer, a thermometer and a condenser: 28.8 grams of monopentaerythritol, 187.1 grams of GE9S, 18.3 grams of n-butylacetate and 0.3550 grams of Tin (II) 2-ethylhexanoate. The mixture was heated to a temperature of about 180° C. for about 5.5 hours till the GE9S was converted to an epoxy group content of about 29 mmol/kg. After cooling down the polyether had a solids content of about 95%.

Example 23

Polyether Resin

The following constituents were charged to a reaction vessel equipped with a stirrer, a thermometer and a condenser: 28.8 grams of monopentaerythritol, 189.4 grams of GE9H, 18.5 grams of n-butylacetate and 0.3572 grams of Tin (II) 2-ethylhexanoate. The mixture was heated to a temperature of about 180° C. for about 4 hours till the GE9H was converted to an epoxy group content of about 27 mmol/kg. After cooling down the polyether had a solids content of about 95%.

Example 24 Comparative

Polyether Resin

The following constituents were charged to a reaction vessel equipped with a stirrer, a thermometer and a condenser: 29.0 grams of monopentaerythritol, 136.7 grams of GE5, 14.0 grams of n-butylacetate and 0.3597 grams of Tin (II) 2-ethylhexanoate. The mixture was heated to a temperature of about 180° C. for about 5.7 hours till the GE5 was converted to an epoxy group content of about 27 mmol/kg. After cooling down the polyether had a solids content of about 94%.

Formulation of the Clear Coats

A clear coat is formulated with one of the polyether (from examples 21, 22, 23 or 24, the curing agent (HDI, Desmodur N3390), the thinner (Methyl Amyl Ketone), the levelling agent (BYK-331) and the catalyst (dibutyltin dilaurate, DBTDL) according to the amounts indicated in table 21.

TABLE 21

Clear coats, formulations

| CEP-Example | Binder (ID) | Binder (g) | HDI (g) | BYK 10 wt % (g) | DBTDL 1 wt % (g) | Thinner (g) |
|---|---|---|---|---|---|---|
| CEP-21 | From Example 21 | 40.1 | 30.7 | 0.47 | 1.03 | 15.1 |
| CEP-22 | From Example 22 | 40.0 | 33.0 | 0.48 | 1.07 | >12.5 |
| CEP-23 | From Example 23 | 40.0 | 32.5 | 0.48 | 1.06 | 17.7 |
| CEP-24 | From Example 24 | 40.1 | 42.9 | 0.54 | 1.20 | 17.7 |

Characterization of the Clear Coats

The clearcoat formulations (from table 21) are barcoat applied on degreased Q-panel, optionally on basecoated Q-panel. The panels are dried at room temperature after a preliminary stoving at 60° C. for 30 min. Clear coats have been characterized among others by measuring the Koenig hardness development (see table 22).

TABLE 22

Clear coats, drying (curing) properties

| | CEP-21 | CEP-22 | CEP-23 | CEP-24 |
|---|---|---|---|---|
| | 1°/Koenig Hardness (Degreased Q panels) (sec) | | | |
| 6 hours | 8 | 10 | 11 | 10 |
| 24 hours | 10 | 11 | 47 | 42 |
| 7 days | 18 | 20 | 94 | 122 |
| | 2°/Koenig Hardness (Basecoated Q panels) (sec) | | | |
| 6 hours | 7 | 8 | 7 | 8 |
| 24 hours | 8 | 8 | 14 | 17 |
| 7 days | 12 | 13 | 34 | 48 |

Observation (see table 22): significant improvement (quicker hardness development) is observed when replacing Cardura E10P or GE9S by GE9H for the polyether cooking. Early hardness improvement on degreased Q-panels is better for example CEP-23 than for example CEP-24.

Example 25

Preparation for Vacuum Infusion of Composite Structures

A resin for vacuum infusion of large structures such as yacht and wind turbines was prepared by mixing 27.7 part by weight of curing agent blend and 100 part of epoxy resins blend described here:

Epoxy resins blend: 850 part by weight Epikote 828 and 150 part of glycidyl neononanoate, GE9H.

Curing Agent blend: 650 part by weight of Jeffamine D230 and Jeffamine D230 is a polyoxyalkyleneamines available from Huntsman Corporation. Epikote 828 is an epoxy resin available from Momentive Specialty Chemicals.

Example 26

Example of Trowellable Floor and Patching Compound

The ingredients presented in the table 23 below were mixed for the preparation of a trowellable flooring compound

TABLE 23

Preparation of a trowellable flooring compound

| | Weight (parts) | Volume (parts) | Supplier |
|---|---|---|---|
| BASE COMPONENT | | | |
| EPIKOTE 828LVEL | 63.2 | 126.3 | Momentive |
| GE9H | 11.1 | 22.3 | |
| Byk A530 | 4.8 | 13.4 | Byk Chemie |
| Mix the additives into the EPIKOTE resin before filler addition | | | |
| Total | 79.1 | 162.0 | |
| FILLERS | | | |
| Sand 1-2 mm | 582.3 | 496.4 | SCR Sibelco |
| Sand 0.2-0.6 mm | 298.4 | 254.4 | SCR Sibelco |
| Total | 880.7 | 750.8 | |
| Disperse into the base component using a concrete mixer | | | |
| CURING AGENT COMPONENT | | | |
| EPIKURE F205 | 40.2 | 87.2 | Momentive |
| Total | 40.2 | 87.2 | |
| Mix the curing agent well with the EPIKOTE resin base and Fillers before application | | | |
| Total formulation | 1000.0 | 1000.0 | |

Example 27

Formulation for a Water Based Self-leveling Flooring

The ingredients presented in the table 24 below were mixed for the preparation of a waterbased self leveling flooring system.

TABLE 24

Preparation of a waterbased self leveling flooring system

| | Weight (parts) | Supplier | Comment |
|---|---|---|---|
| CURING AGENT COMPONENT (A) | | | |
| EPIKURE 8545-W-52 (HEW = 320 g/eq) | 164.00 | Momentive | |
| EPIKURE 3253 | 4.00 | Momentive | Accelerator |
| BYK 045 | 5.00 | BYK CHEMIE | defoamer |
| Antiterra 250 | 4.00 | BYK CHEMIE | Dispersing |
| Byketol WS | 5.00 | BYK CHEMIE | Wetting agent |
| Bentone EW (3% in water) | 20.00 | Elementis | Anti-settling |
| Mix the additive into the EPIKURE curing agents before filler addition | | | |
| Titanium dioxide 2056 | 50.00 | KronosTitan | |
| Disperse the pigment for 10 minutes at 2000 rpm. | | | |
| EWO-Heavy Spar | 195.00 | Sachtleben Chemie | Barium sulphate |
| Quartz powder W8 | 98.00 | Westdeutsche Quarzwerke | |
| Disperse fillers at 2000 rpm for 10 minutes | | | |
| Water | 55.00 | | |
| Sand 0.1-0.4 min | 400.00 | Euroquarz | |
| Total component A | 1000.00 | | |
| RESIN COMPONENT (B) | | | |
| EPIKOTE 828LVEL | 81.00 | Momentive | |
| GE9H | 19.00 | | |
| Mix (B) into (A) | | | |
| Total formulation A + B | 1081.00 | | |

| Formulation characteristics | |
|---|---|
| Fillers + Pigment/Binder ratio | 3.9 by weight |
| PVC | 37.7% v/v |
| Density | 1.9 g/ml |
| Water content | 12.5% m/m |

The invention claimed is:

1. A composition of α,α-branched alkane carboxylic glycidyl esters from butene oligomers, comprising a glycidyl ester mixture of neo-acid based on dimer or trimer of butene having both blocked isomers and highly branched isomers wherein a sum of a concentration of the blocked isomers and of the highly branched isomers is at least 60% weight based on the weight of the composition, wherein a blocked isomer comprises neo-acids having tertiary or quaternary carbon atoms in the β position and a highly branched isomer comprises neo-acids having at least 5 methyl groups, wherein the glycidyl ester mixture comprises 2,2-dimethyl 3,3-dimethyl pentanoic acid glycidyl ester in 10 to 14 weight %, 2-methyl 2-isopropyl 3-methyl butanoic acid glycidyl ester in 20 to 28 weight % and 2-methyl 2-ethyl 3,3-dimethyl butanoic acid glycidyl ester in 17 to 22 weight % based on the weight of the glycidyl ester mixture, wherein the total amount of the glycidyl ester mixture is 100 weight %.

2. A binder composition for paints or adhesives comprising the composition of claim 1 as a reactive diluent or as a monomer.

3. A resin comprising the composition of claim 1 wherein the resin is selected from the group consisting of a polyester polyol resin, an acrylic polyol resin, a polyether polyol resin, or an epoxy resin formulation.

4. A composition of α,α-branched alkane carboxylic glycidyl esters from butene oligomers, comprising a glycidyl ester mixture of neo-acid based on dimer or trimer of butene having both blocked isomers and highly branched isomers wherein a sum of a concentration of the blocked isomers and of the highly branched isomers is at least 60% weight based on the weight of the composition, wherein a blocked isomer comprises neo-acids having tertiary or quaternary carbon atoms in the β position and a highly branched isomer comprises neo-acids having at least 5 methyl groups, wherein the glycidyl ester mixture comprises 2,2-dimethyl 3-methyl 4-methyl pentanoic acid glycidyl ester in 10 to 18 weight % and 2,2-dimethyl 4,4-dimethyl pentanoic acid glycidyl ester in 15 to 22 weight % based on the weight of the composition.

5. A binder composition for paints or adhesives comprising the composition of claim 4 as a reactive diluent or as a monomer.

6. A resin comprising the composition of claim 4 wherein the resin is selected from the group consisting of a polyester polyol resin, an acrylic polyol resin, a polyether polyol resin, or an epoxy resin formulation.

\* \* \* \* \*